United States Patent
Lankton et al.

[11] Patent Number: 6,118,038
[45] Date of Patent: Sep. 12, 2000

[54] ARRANGEMENT AND PROCESS FOR INDIRECT HEAT EXCHANGE WITH HIGH HEAT CAPACITY FLUID AND SIMULTANEOUS REACTION

[75] Inventors: Steven P. Lankton, Wheeling; Joseph E. Zimmermann; Robert C. Mulvaney, III, both of Arlington Heights, all of Ill.

[73] Assignee: UOP LLC, Des Plaines, Ill.

[21] Appl. No.: 09/149,615

[22] Filed: Sep. 8, 1998

[51] Int. Cl.$^7$ .............................. C10G 35/04; C07G 5/327
[52] U.S. Cl. .................. 585/922; 585/911; 585/654; 208/134
[58] Field of Search ...................... 585/654, 911, 585/922; 208/134

[56] References Cited

U.S. PATENT DOCUMENTS

| | | | |
|---|---|---|---|
| 4,549,032 | 10/1985 | Moeller et al. | 585/445 |
| 5,130,106 | 7/1992 | Koves et al. | 422/216 |
| 5,385,122 | 1/1995 | Stalport et al. | 122/511 |
| 5,405,586 | 4/1995 | Koves | 422/218 |
| 5,525,311 | 6/1996 | Girod et al. | 422/200 |

FOREIGN PATENT DOCUMENTS

| | | |
|---|---|---|
| 2028297 | 6/1970 | Germany . |
| 2170898A | 8/1986 | United Kingdom . |

*Primary Examiner*—Walter D. Griffin
*Assistant Examiner*—Tam M. Nguyen
*Attorney, Agent, or Firm*—John G. Tolomei

[57] ABSTRACT

A channel reactor arrangement and a process that uses a high heat capacity heat exchange liquid to indirectly heat or cool by indirect heat exchange. The channel reactor arrangement maintains a pressure gradient through the channels and a pressure differential between the reaction channels and the heat exchange channels at all points to preserve the integrity of the plates defining the channels and to prevent any leakage of high heat capacity liquids into the reaction channels. The system brings the efficiency of plate reactor arrangements to the effectiveness of high heat capacity heat exchange fluids such as molten salts and liquid metals. The process overcomes the problem of low heat exchange pressure drop in combination with high reactant pressure drop by creating a negative pressure differential from reactant channels to the heat exchange channels. Proper control of the pressure drop maintains a positive pressure differential at all locations between the reactant channels and heat exchange channels to prevent any backflow of the heat exchange fluid into the reactant channels while maintaining the overall pressure differential between the channels within suitable limits for plate reactor arrangements. Highly exothermic processes such as oxidation reactions or endothermic processes such as dehydrogenation achieve the most benefit from this invention.

14 Claims, 11 Drawing Sheets

6,118,038

ARRANGEMENT AND PROCESS FOR INDIRECT HEAT EXCHANGE WITH HIGH HEAT CAPACITY FLUID AND SIMULTANEOUS REACTION

FIELD OF THE INVENTION

This invention relates generally to the use of high heat capacity heat transfer fluids such as molten salts and liquid metals for indirect heat exchange and the heating of reactants to control temperature conditions in a reaction process.

BACKGROUND OF THE INVENTION

In many industries, like the petrochemical and chemical industries, contact of reaction fluids with a catalyst in a reactor under suitable temperature and pressure conditions effects a reaction between the components of one or more reactants in the fluids. Most of these reactions generate or absorb heat to various extents and are, therefore, exothermic or endothermic. The heating or chilling effects associated with exothermic or endothermic reactions can positively or negatively affect the operation of the reaction zone. The negative effects can include among other things: poor product production, deactivation of the catalyst, production of unwanted byproducts and, in extreme cases, damage to the reaction vessel and associated piping. More typically, the undesired effects associated with temperature changes will reduce the selectivity or yield of products from the reaction zone.

Many arrangements seek to overcome the negative effects of endothermic chilling by supplying heat to the reaction or of exothermic heating by removing heat from the reaction. More traditional methods employ multiple stages of heating between adiabatic reaction stages. Other methods use in-situ heating via simultaneous reactions or indirect heat exchange to maintain an isothermal or other temperature profile within the reaction zone. U.S. Pat. No. 5,525,311 provides an example of indirect heat exchange with a heat exchange fluid to control the temperature profile within a reaction zone.

A variety of processes can employ indirect heat exchange with a reaction zone to control temperature profiles within the reaction zone. Common examples of hydrocarbon conversion reactions include: the aromatization of hydrocarbons, the reforming of hydrocarbons, the dehydrogenation of hydrocarbons, the oxidation of hydrocarbons and the alkylation of hydrocarbons.

It is known to accomplish indirect heat exchange for processes with thin plates that define reaction and heat exchange channels. The channels alternately retain catalyst and reactants in one set of channels and a heat transfer fluid in adjacent channels for indirectly heating or cooling the reactants and catalysts. Heat exchange plates in these indirect heat exchange reactors can be flat or curved and may have surface variations such as corrugations to increase heat transfer between the heat transfer fluids and the reactants and catalysts. Many hydrocarbon conversion processes will operate more advantageously by maintaining a temperature profile that differs from that created by the heat of reaction. In many reactions, the most beneficial temperature profile will be obtained by maintaining substantially isothermal conditions. In some cases, a temperature profile directionally opposite to the temperature changes associated with the heat of reaction will provide the most beneficial conditions. For such reasons it is generally known to contact reactants with a heat exchange medium in cross flow, cocurrent flow, or countercurrent flow arrangements. A specific arrangement for heat transfer and reactant channels that offers more complete temperature control can again be found in U.S. Pat. No. 5,525,311; the contents of which are hereby incorporated by reference. Other useful plate arrangements for indirect heat transfer are disclosed in U.S. Pat. No. 5,130,106 and U.S. Pat. No. 5,405,586.

In addition to plate arrangements high heat capacity heat transfer fluids have long provided benefits for improving temperature control in reactions. High heat capacity heat transfer fluids are used in several industries to provide cooling for shell and tube heat exchanger arrangements. Suitable types of high heat capacity fluids include alkali liquid metals such as sodium, lithium, and potassium and include molten salts such as nitrates and carbonates. These heat transfer fluid combine high heat capacity with high thermal conductivity. British patent 2170898 generally discloses the use of sodium as a heat transfer medium in high temperature reactions including heat recovery from furnace installations, high pressure nuclear reactors, coal gasification, coal conversion, and water disassociation. U.S. Pat. No. 4,549,032 discloses the use of molten salt as an indirect heat transfer medium with a dehydration of styrene. German patent DE 2028297 discloses the use of an alkaline metal as a beat transfer medium in a process for producing alkenes and aromatics by cracking aliphatic hydrocarbons. The liquid metals are specifically used due to their high heat transfer capacity that permits utilization of small heating surfaces.

One problem with the use of high heat transfer and heat capacity fluids as heat transfer fluids is the need to maintain absolute segregation between the heat transfer fluid and the reactants. The molten salts and liquid metals, used to provide most high capacity heat transfer fluids, typically act as catalyst poisons. Leakage of the high heat capacity stream across the narrow reaction channels can result in premature or immediate catalyst deactivation. Depending upon its composition, such heat transfer fluids may immediately deactivate and/or permanently kill the catalyst. Minute concentrations of the various molten salts or liquid metals can bring about such catastrophic catalyst problems. In many cases even the most minor amounts of leakage of such high heat capacity heat transfer fluids from the heat exchange channels to the reaction channels can quickly shut down a process. Therefore, successful processes must prevent any leakage from the heat exchange channels to the reaction channels when using most catalysts since they are likely to have a high sensitivity to the high capacity heat transfer fluids.

It is therefore, an object of this invention to improve the efficiency of heating reactants in processes and heat transfer arrangements that use thin plate arrangements.

It is a further object of this invention to use high heat capacity heat transfer fluids in combination with thin plate elements having a high heat transfer capacity.

BRIEF SUMMARY OF THE INVENTION

This invention seeks to combine the heat transfer advantages of high heat capacity heat transfer fluids with the high heat flux obtained across channels defined by thin heat transfer plates. The invention operates by circulating a high heat transfer capacity liquid through heat transfer channels and maintaining a pressure drop over the flow path of the high heat transfer capacity liquid through the channels. Similarly, narrow channels defined by the same heat transfer plates that define the heat exchange channels contain a reactant fluid. The reactant fluid passes through the channels and creates a pressure drop over its flow path through the reaction channels.

This invention can also maintain a positive pressure drop from the reaction channels to the heat exchange channels that prevents any leakage of the heat transfer fluid from deactivating catalyst in the reaction channels. Accordingly, the process and apparatus of this invention can also operate in a manner such that the pressure differential between the reaction channels and the heat exchange channels is at all times positive and the heat exchange fluid cannot enter the reaction channels. Where necessary the invention adjusts the pressure drop through the heat exchange channels to provide suitable back pressure to the reaction channels and avoid any pressure differential that exceeds the desired pressure loading across the thin heat transfer plates. The need for pressure adjustment in the heat exchange channels arises from the relatively low pressure drop created by the high heat capacity fluid as opposed to the relatively high pressure drop created by the passage of reactants through catalyst filled channels. This variance in pressure interferes with protecting the catalyst from the contamination or deactivation by leakage of the heat transfer fluid. Advantageous use of the high heat capacity heat transfer fluids typically results in a relatively low flow velocity. The low flow velocity from the heat transfer fluids typically raises minimal pressure drop through the heat exchange channels. Operating the catalyst channels at a sufficient pressure to overcome their inherently higher pressure drop and provide the desired positive pressure differential can create excessively high pressure differentials at points in the reaction channels and typically at the reaction channel inlets. Excessively high pressure differentials will deform the typically thin channel walls and can lead to leakage. Therefore, the overall pressure in the reaction channels can not simply increase to maintain the positive pressure differential without increasing the maximum pressure differential between the heat exchange and the reaction channels to unacceptably high levels.

The pressure balancing problems are compounded by operating a plate exchanger design with relative cross-current or countercurrent flow between the heat exchange channel and the reaction channels. By moving the heat transfer fluid and the reaction fluid in cocurrent flow there will be a simultaneous decrease in pressure on both sides of the heat transfer plates as the pressure drop reduces the pressure level in both the heat exchange channels and the reaction channels. This invention further facilitates the use of the high heat capacity heat transfer fluid in a plate channel arrangement by creating enough pressure drop into the heat exchange channels to maintain a higher relative pressure at all points in the reaction channels without raising the pressure differential from the reaction channels to the heat transfer channels that will cause damage to thin heat transfer plates.

Control of pressure drop through the heat exchange channels can provide balancing of the pressure differential between the heat exchange channels and the reaction channels. Inert material may be added to the heat exchange channels to provide additional pressure drop. The additional pressure drop raises the pressure in the heat exchange channels to compensate for any higher inlet pressure required in the reaction channels for pressure drop reasons. Pressure drop in the heat exchange channels may also be increased by varying the relative width of the channels. The different width of the respective channels may be uniform such the heat exchange channels have a smaller relative constant width than the reaction channels. The width of the channels may also vary over the length of the channels to vary the heat transfer as well as the pressure drop over the length of the channels.

Suitable plate arrangements may also incorporate secondary plates that enlarge the reaction channels relative to the heat exchange channels. Most advantageously the secondary plates contain perforations to freely communicate reactants across the entire width of any relatively wide reaction channel while also improving heat exchange by conduction of heat from imperforate channel boundary plates to the perforated plates occupying the reaction channels. Those skilled in the art will recognize other variations in plate configurations that can provide additional benefits to the integration of the heating and reaction channels.

Suitable heat exchange fluids comprise metals or salts that maintain a liquid state at the desired heat exchange conditions of the process. Preferably, the molten metal selected from the group consisting of sodium, potassium, lithium, lead, antimony, bismuth, and mixtures thereof. Mixtures of the above metals may form particularly useful eutectic mixtures.

The high heat capacity heat transfer fluids contemplated for use in this invention are best characterized by their Prandtl number (Pr). Pr measures the ratio of kinematic viscosity to thermal diffusivity. The heat transfer performance of the fluid applicable to this invention increase with decreasing Pr. For typical hydrocarbon stream in a carbon number range of from 1 to 14 the Pr will be in a range of from 0.5 to 1.0. The heat transfer fluids to which this invention applies will have a Pr of 0.1 or less and preferably of Pr of 0.05 or less.

Accordingly, in one embodiment this invention is a process for contacting reactants with a catalyst in a reaction zone and indirectly heating or cooling the reactants by contact with a heat exchange liquid having a high heat capacity. The process passes a reactant stream through a plurality of narrow reaction channels defined by principal spaced apart plates and establishes a first pressure gradient through the narrow reaction channels. The reactant stream chemically reacts in at least a portion of the narrow reaction channels to produce a reacted stream. A liquid heat exchange fluid having a Pr of not more than 0.1 passes through a plurality of narrow heat exchange channels defined by the principal plates and establishes a second pressure gradient through the narrow heat exchange channels. The heat exchange channels indirectly exchange heat with the reactant stream across the plates in the portion of the reaction channels. A positive pressure differential from the reaction channels to the heat exchange channels exists at all locations across the principal plates. The process recovers a reacted stream from the reaction channels.

In a more limited embodiment this invention is a process for contacting reactants with a catalyst in a reaction zone and indirectly heating or cooling the reactants by contact with a heat exchange liquid having a high heat capacity. The process comprises passing a reactant stream through a plurality of narrow reaction channels defined by principal spaced apart plates and into contact with catalyst particles retained in at least a portion of the reaction channels to produce a first pressure gradient through the narrow reaction channels of at least 138 kPA (20 psi). The reactant stream catalytically reacts in at least a portion of the narrow reaction channels to produce a reacted stream. A heat exchange liquid having a Pr of not more than 0.1 passes through a plurality of narrow heat exchange channels defined by the principal plates in an arrangement that interleaves the reaction channels with the heat exchange channels. The heat exchange channels contain a flow restricting medium to produce a second pressure gradient through the heat exchange channels that is less than the pressure gradient through the reaction channels. The process indirectly exchanges heat with the reactant stream across the plates in the portion of the reaction channels and maintains a positive pressure differential of less than 345 kPA (50 psi) from the reaction channels to the heat exchange channels at all locations across the principal plates while recovering the reacted stream from the reaction channels.

In another embodiment this invention is an apparatus for contacting reactants with a catalyst in a reaction zone and indirectly heating or cooling the reactants by contact with a heat exchange liquid having a high heat capacity. The apparatus comprises a plurality of alternate reaction channels and heat exchange channels defined by a plurality of primary plates to have a reactant inlet at one end of the reaction channels, a reactant outlet at a second and opposite end of the reaction channels, an exchange fluid inlet at one end of the heat exchange channels and an exchange fluid outlet at the opposite end of the heating channels. A flow restrictor in the heat exchange channels restricts flow through the heat exchange channels relative to flow through the reaction channels when in an open channel condition.

Additional embodiments, arrangements, and details of this invention are disclosed in the following detailed description of the invention.

DETAILED DESCRIPTION OF THE INVENTION

Figure 1:
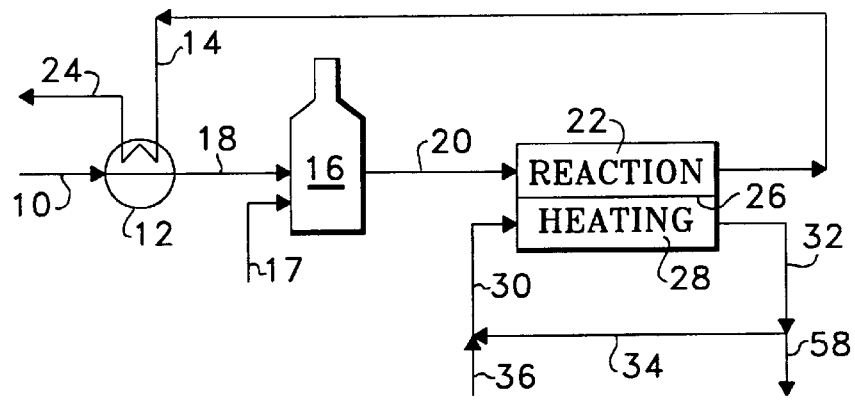
FIG. 1 is a schematic flow diagram of a reaction zone, heating zone, heat exchanger, and charge heater arrangement in accordance with this invention.

The presence of narrow heating channels for containing reaction and heating functions constitutes an essential requirement of this invention. The heat exchange and reaction channels may take on a many different configurations that suit the particular process and heating fluid. This invention is useful for plate channel arrangements with or without restrictions in the heat exchange channels or reaction channels.

Nevertheless, the reaction channels will typically contain a catalyst a portion along a continuous length of the channel or portion of the channels. A catalyst free section of the reaction channels may serve to preheat the reactants upstream of a catalytic section or cool the reacted components downstream of reaction section. In vertically extending channels, short loading of particulate catalyst in the reaction channels can provide a space above or below the catalyst reaction section that preheats feed or cools reactants. This invention is most beneficially used in combination with particulate catalysts. Particulate catalysts impose the highest pressure drop through the channels and as a result require more balancing of pressure via restriction in the heat exchange channels. However, as an alternate to a particulate catalyst, the catalyst may also be coated on the surface of the plates in the various reforming zones. It may be particularly advantageous to coat catalyst onto the plates to provide an upper catalytic section and a lower catalyst-free section that is maintained in heat exchange relationship across the channel defining plates with the heat exchange section.

Requirements of this process for compatibility with a plate exchanger arrangement will typically require that there be a relatively low $\Delta T$ between the exothermic and endothermic reaction zones along with the relatively low $\Delta P$ across the plate sections. Differential temperatures of 200° C. or less are preferred for this invention. Differential pressures preferably will not exceed 0.7 MPa and more preferably 0.35 MPa. Many reactions for the production of hydrocarbon and chemical products meet these requirements.

The reaction zones for the process of this invention may indirectly contact the reactants with the heat exchange fluid in any relative direction. Thus, the flow channels and inlets and outlets of the reaction zones may be designed for cocurrent, countercurrent, or cross-flow of reactant fluid relative to the heat exchange fluid. Regardless of the relative flow direction between the heat exchange and the reaction channels the positive pressure drop between the reaction channels and heat exchange channels will preferably be maintained. Preferred process arrangements for practicing this invention will pass reactants in cocurrent flow or countercurrent flow to maximize contact with the heat exchange fluid for heat producing reaction zones. Cross-flow of reactants may sometimes be used to minimize the overall pressure drop associated with the flow of reactants through the reactor. For this reason, a cross-flow arrangement can be used to provide the reactants with a shorter flow path across the reaction zone while still providing the desired positive pressure drop.

The shorter flow path reduces overall pressure drop of the reactants as they pass through catalyst particles retained in the reactor. Lower pressure drops can have a two-fold advantage in the processing of many reactant streams. Increased flow resistance i.e., pressure drop, can raise the overall operating pressure of a process. In many cases, product yield or selectivity is favored by lower operating pressure so that minimizing pressure drop will also provide a greater yield of desired products.

This invention has application to any exothermic or endothermic process. Catalytic dehydrogenation is an example of an endothermic process. In catalytic dehydrogenation, a feedstock is admixed with a recycle stream comprising hydrogen and contacted with catalyst in a reaction zone. Feedstocks for catalytic dehydrogenation are typically petroleum fractions or liquid petroleum gases comprising aromatic or paraffinic hydrocarbons. The dehydrogenation of ethyl benzene to produce styrene is well known. Paraffinic feedstocks ordinarily have from about 3 to about 18 carbon atoms. Particular feedstocks will usually contain light or heavy paraffins. A catalytic dehydrogenation reaction is normally effected in the presence of catalyst particles comprised of one or more Group VIII noble metals (e.g., platinum, iridium, rhodium, palladium) combined with a porous carrier such as a refractory inorganic oxide. Alumina is a commonly used carrier. Dehydrogenation conditions include a temperature of from about 400° to about 900° C., a pressure of from about 0.01 to 10 atmospheres, and a liquid hourly space velocity (LHSV) of from about 0.1 to 100 $hr^{-1}$. Generally the lower the molecular weight of the feed the higher the temperature required for comparable conversions. The pressure in the dehydrogenation zone is maintained as low as practicable, consistent with equipment limitations, to maximize the chemical equilibrium advantages. The preferred dehydrogenation conditions of the process of this invention include a temperature of from about 400°–700° C. and a pressure from about 0.1 to 5 atmospheres.

The effluent stream from a dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds. Additional information related to the operation of dehydrogenation catalysts, operating conditions, and process arrangements can be found in U.S. Pat. No. 4,677,237; U.S. Pat. No. 4,880,764 and U.S. Pat. No. 5,087,792; the contents of which are hereby incorporated by reference.

An exothermic reaction example that represents a particularly beneficial process application for this invention is in the production of phthalic anhydride (PA) by the oxidation of orthoxylene. The reaction apparatus feeds the orthoxylene feed to distribution manifold that injects an controlled amount of oxygen in admixture with the orthoxylene. Injection of the oxidation compound into the manifold prevents the presence of the orthoxylene and oxygen in explosive proportions. The plate arrangement of the heat exchange reactor quickly dissipates the high heat of reaction associated with the synthesis of the PA. The enhanced temperature control improves product selectivity while also permitting increased throughput.

FIG. 1 shows a typical type of process application for this invention wherein a process stream enters the process arrangement via line 10 and passes through a heat exchanger 12 which recovers heat from a reaction zone effluent stream 14. Partially heated feed from exchanger 12 passes to an optional charge heater 16 via a line 18. A line 17 adds fuel to the charge heater 16. A line 20 carries the heated feedstream into contact with a catalyst in a reaction zone 22 for an endothermic reaction to produce the effluent stream 14 that exits the process downstream of heat exchanger 12 via a line 24. Reaction zone 22 exchanges heat across a heat transfer plate 26 with a heat exchange zone 28. Line 30 passes a heating medium into heating zone 28. After heat exchange in zone 28 line 32 withdraws the cooled heating medium. Optionally line 34 recirculates a portion of the heating medium back to the inlet of the heating zone via a line 34. Cooled heating medium may be withdrawn via a line 38 and returned to the heating zone via a line 36.

Figure 2:
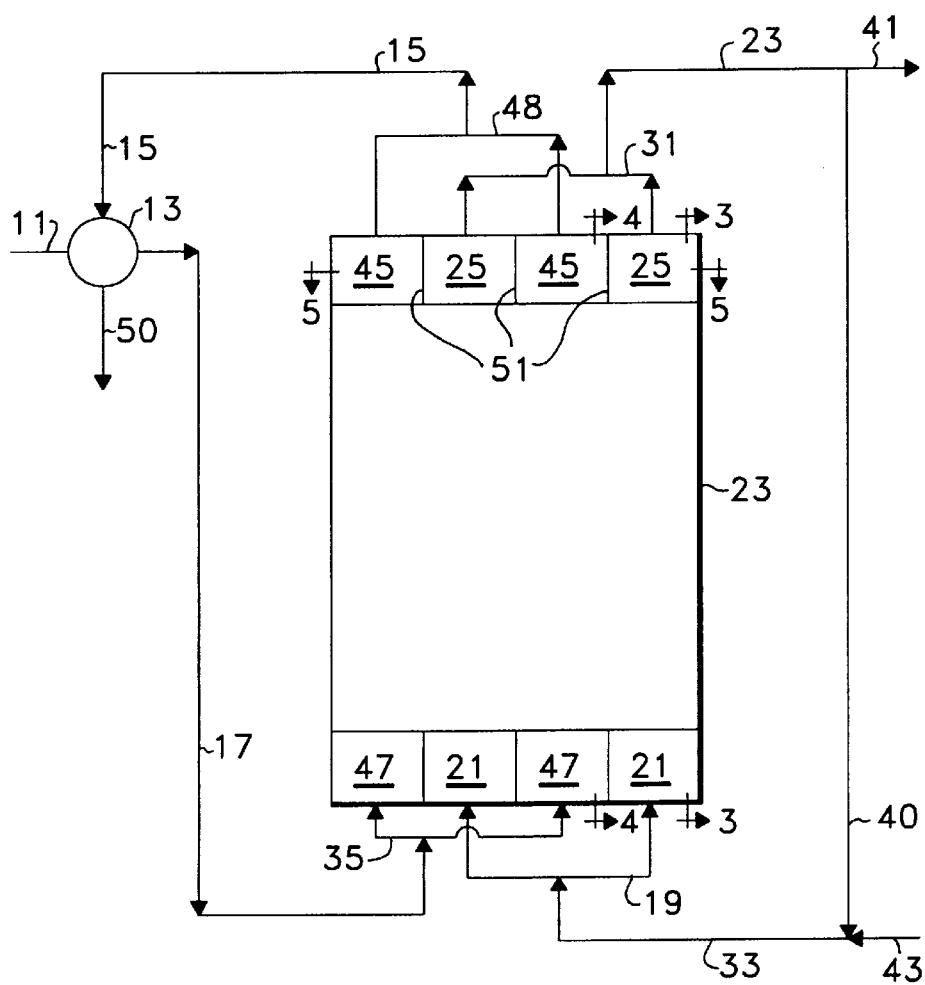
FIG. 2 is a schematic diagram of vertical plate channel exchanger incorporating an arrangement of this invention.
Figure 4:
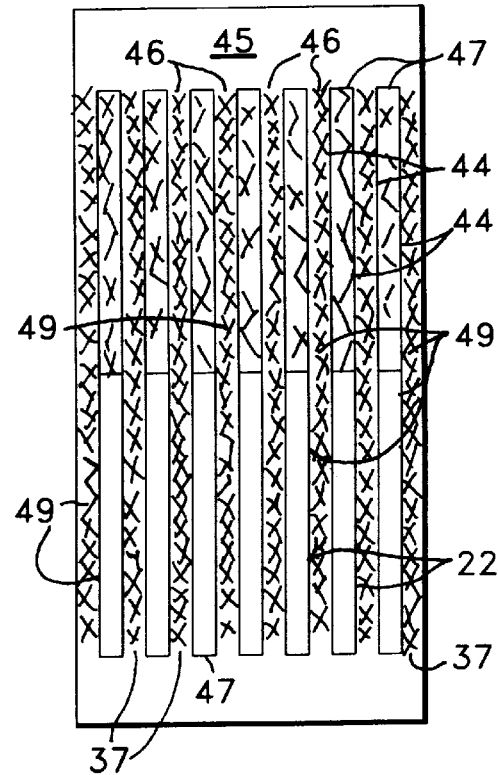
FIG. 4 is a section of the schematic heat exchange reactor shown in FIG. 2 taken at section 4—4.

Considering, for purposes of example, the process and the schematic internals of the reaction zone are further described in the context of a process for the dehydrogenation of detergent range paraffins to olefins. Looking then at FIG. 2, a heavy paraffin dehydrogenation process passes a feedstream comprising normal paraffins in the range of from 3 to 18 carbon atoms to a heat exchanger 13 that heats the incoming feed against the outgoing product stream contained in line 15. Line 17 passes the heated feed to a manifold 35 that distributes the feed to distribution spaces 47. As shown further in FIG. 4, distribution spaces 47 distribute the incoming feed to inlets 37 of reaction channels 49. Thin heat transfer plates 44 separate reaction channels 49 from heat exchange channels 29. Reaction channels 49 contain a particulate material comprising a dehydrogenation catalyst. Hydrogen and the olefin-containing product exit the reaction channels 49 through outlets 46 and enter collection chamber 45. A manifold 48 collects the dehydrogenation zone effluent for transfer to heat exchanger 13 via line 15. Line 50 removes he olefin containing stream for separation and recovery of product.

Figure 3:
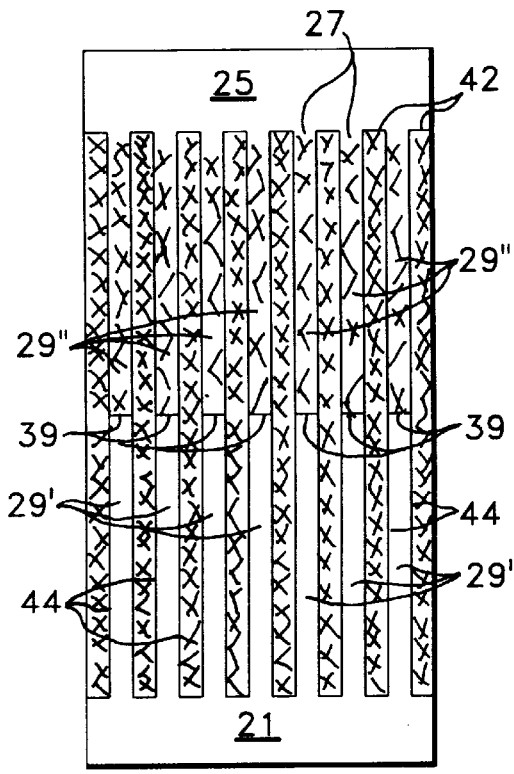
FIG. 3 is a section of the schematic heat exchange reactor shown in FIG. 2 at section

The circulation of a liquid sodium heat transfer fluid through the heat exchange channels maintains an essentially uniform temperature throughout the reaction channels 49. The heated liquid sodium enters the process through a line 43. Heated liquid sodium and recirculated liquid sodium from a line 40 pass via a line 33 into a manifold 19 for distribution to the heat exchange channels 29 via distribution spaces 21. As shown in FIG. 3, the liquid sodium flows upwardly through an open portion 29' of heat exchange channels 29 before contacting a particulate material in an upper portion 29" of heat exchange channels 29. A perforated plate section 39 retains the particles in the upper portion 29' of heat exchange channels 29. It is only necessary to fill a portion of channels 29 to obtain the necessary flow restriction which is provided by the particles retained in section 29". The presence of the flow restriction in only a portion of heat exchange channels 29 brings the pressure drop of the heat exchange fluid on the inlet side of the heat exchange channels within the desired range to balance the pressure in the reaction channels without causing excessive pressure differential across thin plates 44. This balancing maintains a positive pressure drop from the reaction channels 49 to the heat exchange channels 29. Cooled sodium flows out of outlets 27 of heat exchange channels 29 into the collection space 25. A manifold 31 gathers the heat exchange fluid from the collection spaces 25 for delivery to an outlet line 23. A reheat line 41 withdraws a portion of the exiting liquid sodium while recirculation line 41 returns the remaining portion of the liquid sodium to line 33.

Figure 5:
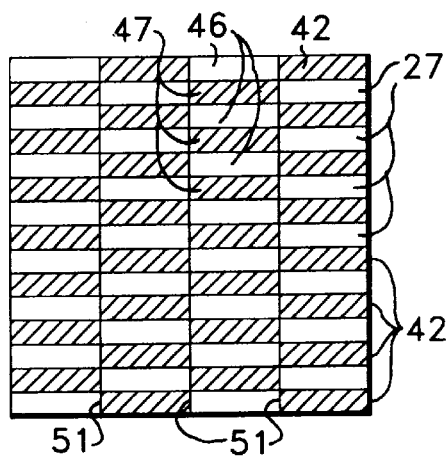
FIG. 5 is a horizontal section of the schematic heat exchange reactor shown in FIG. 2 taken at section 5—5.

FIG. 5 illustrates the arrangement for segregating the flows through the heat exchange channels and the reaction channels. The partition plate 51 segregates the upper portion of the reactor into the collection spaces 25 and the collection spaces 45 associated with the reaction fluid and the heat exchange fluid, respectively. Outlets 27 register with the portion of the collection space 25 that lies directly above.

The tops 42 of the reaction channels 49 are blocked to fluid flow where they coincide with the collection chamber 25. The upper portions 47 of the heat exchange channel that coincide with the collection space 46 are closed to fluid flow. Outlets 46 of the reaction channels remain open only in those portions that register with the collection space 45. The segregation of the flow occurs in an analogous manner on the inlet side of the heat exchange and reaction channels.

Suitable plates for this invention will comprise any plates that allow a high heat transfer rate. Thin plates are preferred and usually have a thickness of from 1 to 2 mm. The plates are typically composed of ferrous or non-ferrous alloys such as stainless steel. Preferred alloys for the plates will withstand extreme temperatures and contain high proportions of nickel and chrome. The plates may be formed into curves or other configurations, but flat plates are generally preferred for stacking purposes. Suitable plate arrangement may use relatively smooth plates with intermediate spacers placed intermittently between the plates to preserve the channel space and to introduce turbulence for promoting heat transfer. Additional elements such as spacers or punched tabs may provide also provide spacing of and turbulence in the channels. Such structures may also provide another form of flow restriction in the heat exchange channels.

A preferred form of the heat exchange elements comprise relatively flat plates having corrugations defined therein. The corrugations that are usually inclined to the flow of reactants and heat exchange fluid. The corrugations serve to maintain spacing between the plates while also supporting the plates to provide a well supported system of narrow channels. Additional details on the arrangement of such plate systems are again shown in U.S. Pat. No. 5,525,311.

Figure 6:
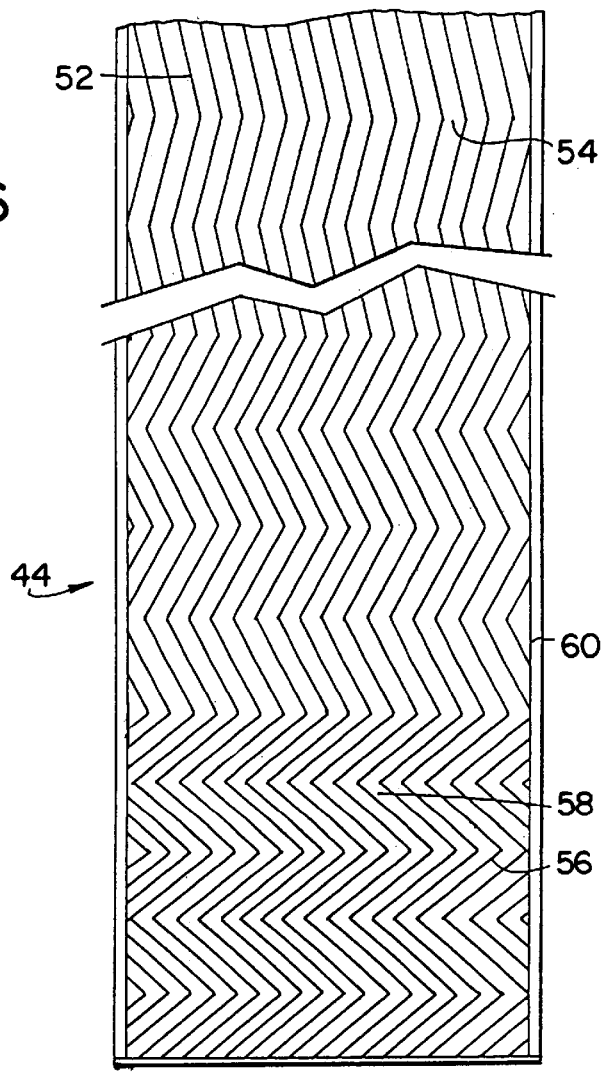
FIG. 6 is a schematic drawing of a flat plate element showing a corrugation pattern.

FIG. 6 shows the preferred corrugation arrangement where the plates 44 that divide the central portion of heat exchange reactor 23 into heat exchange channels and reaction channels are formed by plates having a corrugation arrangement. Again the corrugation pattern can serve to structurally support adjacent plates and promote turbulence for enhancing heat exchange efficiency in the narrow reaction channel. FIG. 6 shows corrugations defined by ridges 52 and valleys 54. The frequency or pitch of the corrugations may be varied as desired to promote any varying degree of turbulence. Therefore, more shallow corrugations as shown by ridges 52 and valleys 54 will produce less turbulence. Whereas greater corrugation pitches, as shown by ridges 56 and valleys 58, may provide increased turbulence where desired. The pitch of the corrugations and the frequency may also be varied over a single heat exchange channel to vary the heat transfer factor in different portions of the channel. The channels may contain a flat portion 60 about their periphery to facilitate closure of the channels about the sides and tops where desired.

Figure 7:
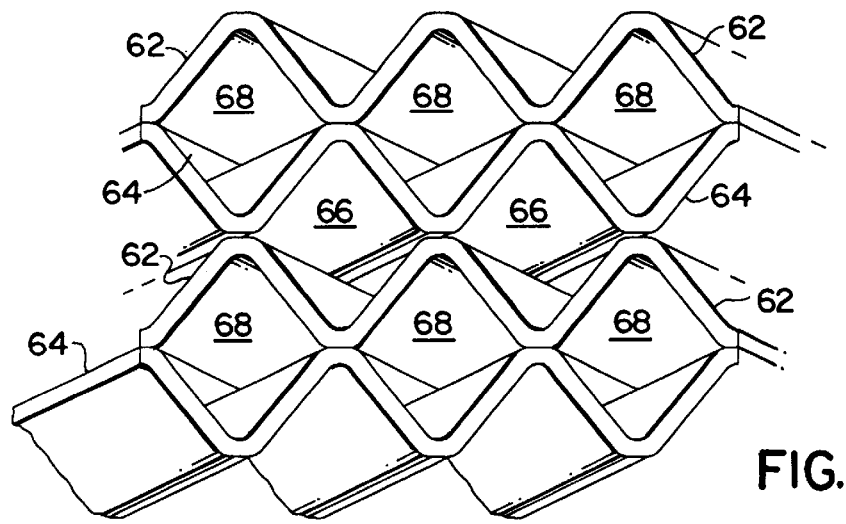
FIG. 7 is an isometric view of corrugated plates forming flow channels.

FIG. 7 shows a typical cross-section of a corrugated plate arrangement wherein the corrugations of plates 62 extend in an opposite direction to the corrugations of plates 64 thereby defining alternate reaction channels 66 and heating channels 68. FIG. 7 illustrates the preferred arrangement of corrugated plates where the herring bone pattern on the faces of opposing corrugated plates extends in opposite directions and the opposing plate faces contact each other to form the flow channels and provide structural support to the plate sections.

Again, the invention relies on relatively narrow channels to provide the efficient heat exchange across the plates. The corrugations maintain a varied channel width defined by the height of the corrugations. Ordinarily, the channel width is less than one inch on average with an average width of less than ½ inch preferred. In the case of corrugations, the average channel width is most practically defined as the volume of the channels per the cross-sectional area parallel to the primary plane of the plates. By this definition corrugations with essentially straight sloping side walls will have an average width that equals half of the maximum width across the channels.

It is also not necessary to the practice of this invention that each reaction channel be alternated with a heat exchange channel. Possible configurations of the reaction section may place two or more reaction channels between each heat exchange channel to reduce the pressure drop on the reaction channel side. When used for this purpose, a plate separating adjacent reaction channels may contain perforations.

Figure 8:
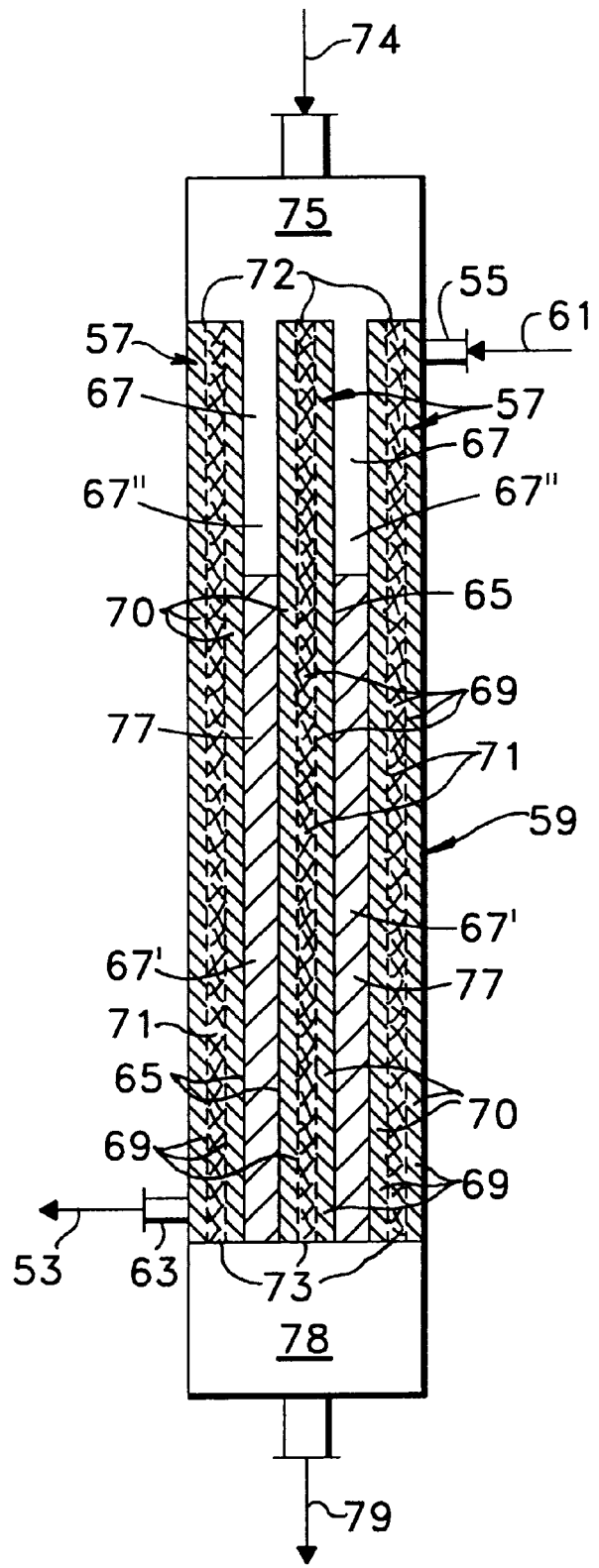
FIG. 8 is a schematic diagram of an alternate vertical plate channel exchanger incorporating an arrangement of this invention.

FIG. 8 depicts a schematic flow arrangement and conceptual reactor details for a process that uses multiple reaction channels for each heat exchange channel. A gas feed enters the process via line 61. The gas feed may first undergo heat exchange in a conventional heat exchanger (not shown) with the reacted stream that exits the process by line 53. An inlet nozzle 55 transfers the incoming feed to a distribution device (not shown) that distributes the entering reactants to reaction channels 57. Imperforate plates 65 define the boundary between the reaction channels 57 and heat exchange channels 67. Contact with catalyst in the reaction channels 57 promotes the conversion of the reactants and the production of the reacted stream that exits reaction channels 57 via a collection device (not shown). The collection device delivers the reacted stream to a nozzle 63 from which line 53 withdraws the reacted stream.

Reaction channels 55 contain perforated plates 69 to facilitate maintaining the spacing of the reaction channels while varying the relative width between reaction channels 55 and heat exchange channels 67. Perforated plates 69 form subchannel spaces 70 to their outside of a central subchannel 71. All of the subchannel spaces typically retain catalyst over some portion of their length. Subchannel spaces 70, may hold the same catalyst or a different catalyst from that located in the central portion 71 between the perforated plates 69. Perforations in plates 69 circulate the reactants between the different subchannel portions. The perforations may be sized to permit only fluid flow while occluding particle permeation or may be sized to permit both fluid and particle movement. The presence of the perforated plates also provides a conductive member that enhances heat transfer over the larger width of the reaction channels.

The reactor arrangement of FIG. 8 particularly suits itself for the loading of particulate catalysts. Upper ends 72 of reaction channels 57 are closed after catalyst loading to prevent the entry of the heat exchange fluid from space 75. Closed bottoms 73 of reaction channels 57 hold catalyst in place and prevent the communication of gas between reaction channels 57 and heat exchange channels 67.

The heat exchange fluid passes via line 74 to a distribution space 75. Distribution space 75 disperses the heat exchange fluid to the plurality of heat channels 67. As the heat exchange fluid flows downwardly through heat exchange channels 67, the large surface area provided by the plates 65 that define the reaction and heat exchange channels efficiently transfer heat to or from the reaction channels 57. Again the heat exchange channel can contain a particulate material or other flow restriction to raise pressure drop through the channels. Optional short loading of the particulate material into a lower portion 67' of channels 67 maintains a particulate free upper section 67" that permits desired adjustment of the pressure drop through the heat exchange channels. A screen material located at the bottom of channels 67 permits flow of the heat exchange fluid while holding any particulate material in place. Collection space 78 gathers the effluent from the heat exchange channels and directs it to line 79 for recycle with heating or cooling of any portion thereof.

Figure 9:
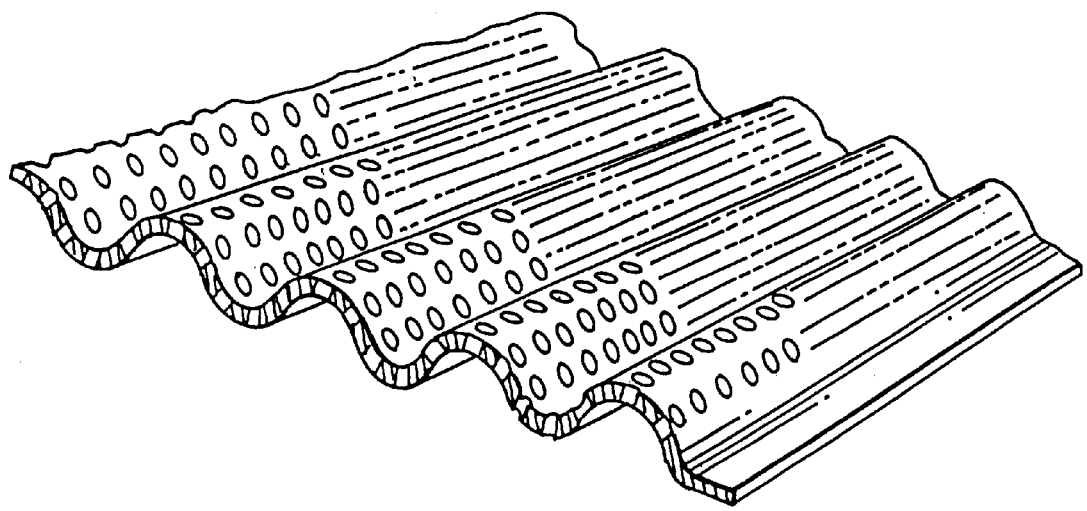
FIG. 9 is an isometric view of a single corrugated plate containing perforations.
Figure 10:
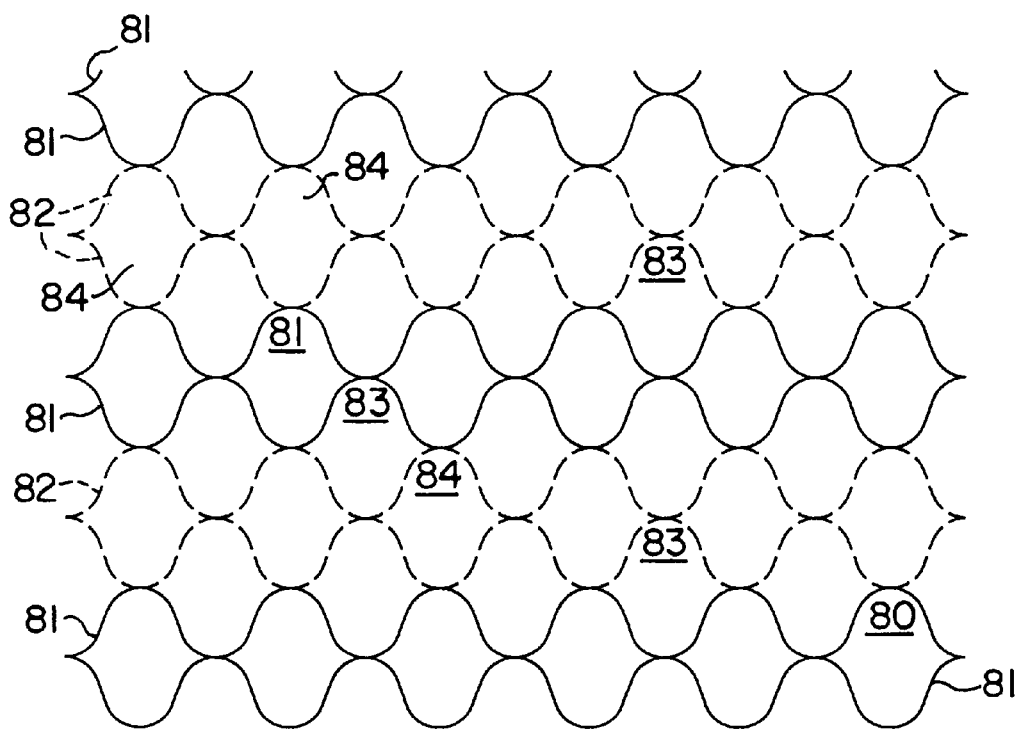
FIG. 10 is a schematic representation of flow channels formed by corrugated primary plates and perforated secondary plates.

FIG. 10 depicts a cross section of an idealized arrangement for the perforated plates and imperforate plates to define the heat exchange and reaction channels of the type shown in FIG. 8. The space between imperforate plates 81 define heat exchange channels 80. The space bordered by one perforated plate 82 and one imperforate plate 81 define the outer subchannels 83 of the reaction channels. The space bordered by both the perforated plates sets the boundary of the inner channels 84 within the reaction channels. FIG. 9 shows a corrugated plate of a type with perforations over its length that is suitable for use on the channel arrangement of FIGS. 8 and 10.

The arrangement of the reaction and the heat exchange channels are susceptible to many additional variations. Distribution chambers along the channel paths may provide sites for intermediate injection of reactants or heat exchange medium. Distribution chambers may be provided at the ends of channels or along the mid points, as desired. One arrangement of such manifolds uses two or more separate stacks of heat exchange plates or "reaction stacks" to conduct different reactions and heat exchange steps in isolated banks. A system of manifolds can pass the isolated reactants and heat exchange fluid to another section of heat exchange channels and reaction channels that again indirectly contact the heat exchange fluid with the reactants. Integration of the manifolds with external pipes can further enhance process control by the intermediate addition or withdrawal of heat exchange fluid or reactants.

EXAMPLE 1

The effect of using the process and channel arrangements of this invention to maintain isothermal conditions was investigated in a hydrocarbon conversion process for the dehydrogenation of light paraffins. A simulation based on the ability of this invention to maintain isothermal conditions was prepared The isothermal conditions that result from this invention were simulated in a dehydrogenation process using a configuration of alternating heating and reaction channels.

The process simulation of preheat and catalytic reaction zone portions is based on the use of a plate heat exchange bundle having 5 layers of catalyst, and a length of about 3.75 m. The plates define the reaction channels which alternate between the heating channels and have a thickness of about 1.2 mm, corrugations with a depth of about 10 mm and a width of about 270 mm. The plates are placed next to each other in an alternating pattern of corrugations, such that the peaks of the corrugations are in contact. The reaction channels and heat exchange channels operate at an average pressure of about 138 kPa (20 psig).

In this process simulation, a feedstream having comprising 71.4 mol % propane, 0.6 mol % propylene, 4.6 mol % lighter hydrocarbons and 23.2 mol % hydrogen passes into a conventional heat exchanger. Conventional heat exchange with the dehydrogenation zone effluent stream raises the feedstream temperature from approximately 40° C. to 510° C. The partially heated feedstream passes to the heat exchange channels in counter current flow with respect to the heat exchange fluid. Indirect heat exchange with a liquid sodium heat exchange fluid against a preheat portion of the reaction channels raises the temperature of the feed to about 600° C. The recovered dehydrogenation zone effluent stream provides the heat exchange fluid for the conventional heat exchanger.

The heated feedstream undergoes dehydrogenation to produce a product stream comprising 41.29 mol % propane, 17.78 mol % propylene, 4.37 mol % lighter hydrocarbons and 36.51 mol % hydrogen. The catalytic reaction section contains a typical dehydrogenation catalyst comprises platinum on an alumina support. Indirect heating from the liquid sodium stream maintains the temperature of the outlet temperature of the product stream at about 608° C. The temperature of the liquid sodium stream varies from an inlet temperature of about 615 to an outlet temperature of about 594. Total pressure drop for the reactants through the reaction channels is about 172 kPa (25 psig) and the total pressure drop of the liquid sodium through the heat exchange channels less than 7 kPa (1 psig).

EXAMPLES 2–4

To more fully illustrate the process and apparatus of this invention and its advantages in an exothermic process application the following examples present the calculated operation a tubular heat exchange type reactor and the calculated operation of different plate channel reactor arrangements of the type depicted in the Figures. All of the examples show the oxidation of orthoxylene to phthalic anhydride. The numerical model uses well established kinetic data and experimentally developed heat transfer data. All of the catalytic data was based on performance parameters for a silicon carbide base material surface coated vanadiumpentoxide having a surface area of 2000 $cm^2$/g. All examples operated to keep the phthalide content in the effluent at less than 1000 ppm in the PA product. The examples also modeled the use of molten salt as the cooling medium. Comparison of the numerical model against published literature for similar modeling studies verified its accuracy.

EXAMPLE 2

Figure 11:
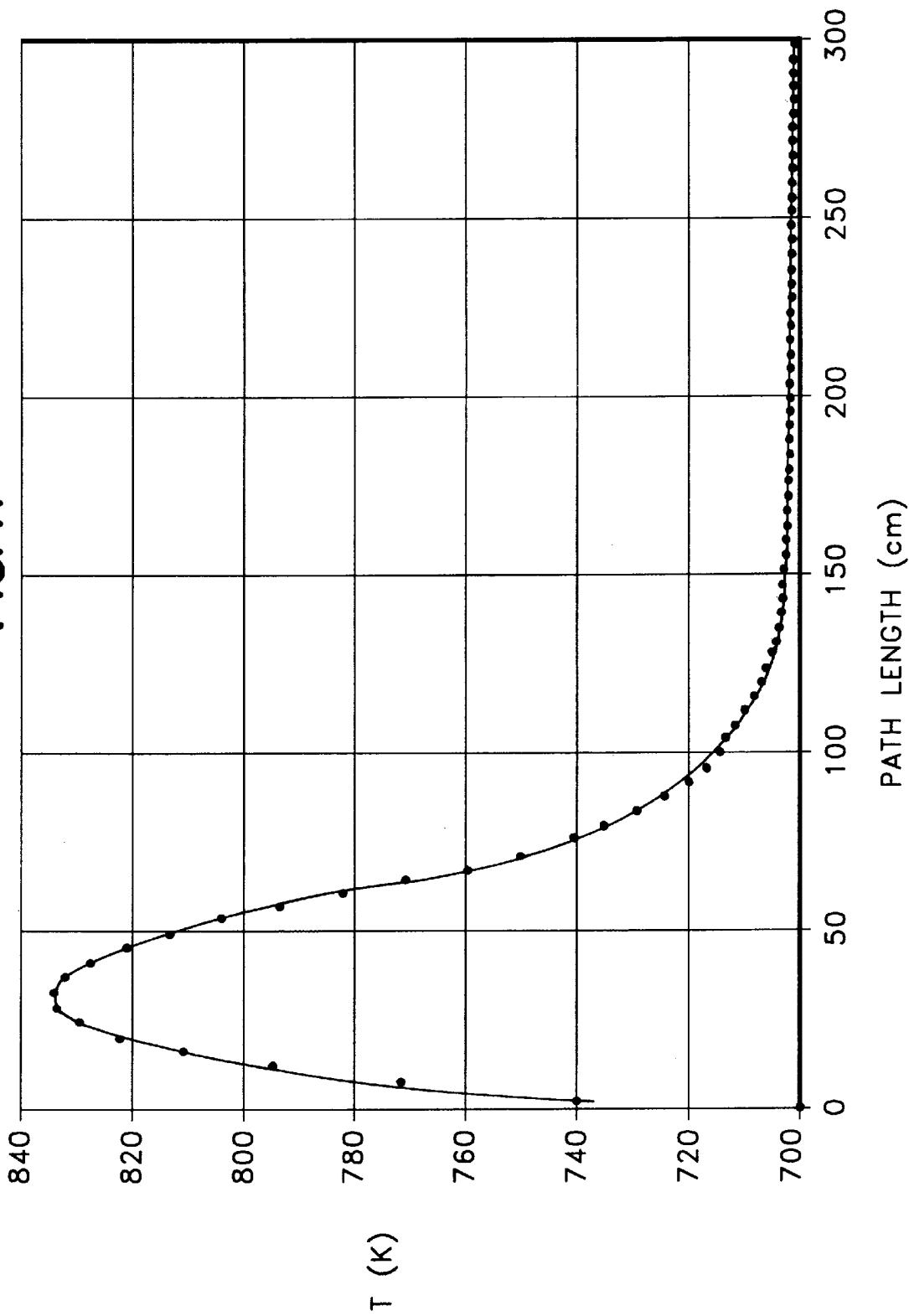
FIGS. 11 and 12 are graphs showing the temperature profile and conversion parameters along the path length of tubes in a tubular arrangement for PA production by orthoxylene oxidation.
Figure 12:
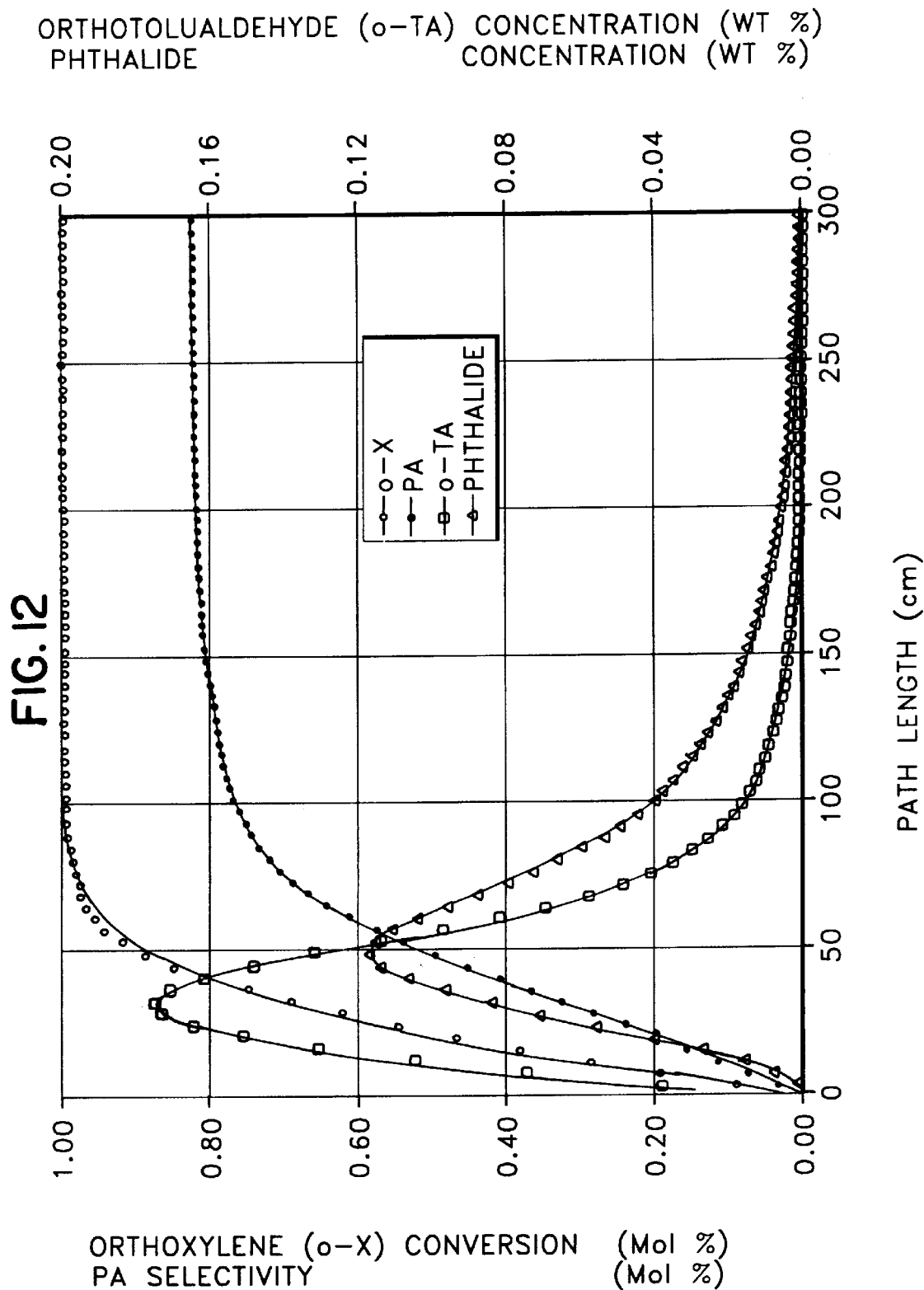

This example is provided to establish the performance of the tubular reactor base case and produced similar results to current industrial tubular reactor performance. In this base case a feedstock of air containing an orthoxylene concentration of 75 g/$Nm^3$ feed passes through a three meter long tube having a diameter of 25 mm at a mass flux rate of 10,000 kg/$m^2$/hr which produces a 0.3 bar pressure drop along the tube. The tubular reactor model uses a ring shaped particle having a diameter of 9 mm. Circulation of a salt bath at a temperature of 698° K. around the shell side of the tubes provide cooling. The feed enters the tubular reactor at a temperature of about 700° K. The final phthalide content in the PA product was below 1000 ppm. FIG. 11 graphically depicts the temperature profile over the length of a representative tube. The tube achieves a peak temperature of about 835° K. within the first 50 cm of its path length. FIG. 12 illustrates an essentially complete conversion of orthoxylene with about the first 100 cm of tube length. As also presented by FIG. 12, continued conversion in the tubes reduces the concentration of orthotolualdehyde and phthalide to levels of less than 1000 ppm while raising the PA selectivity to about 83%.

EXAMPLE 3

Figure 13:
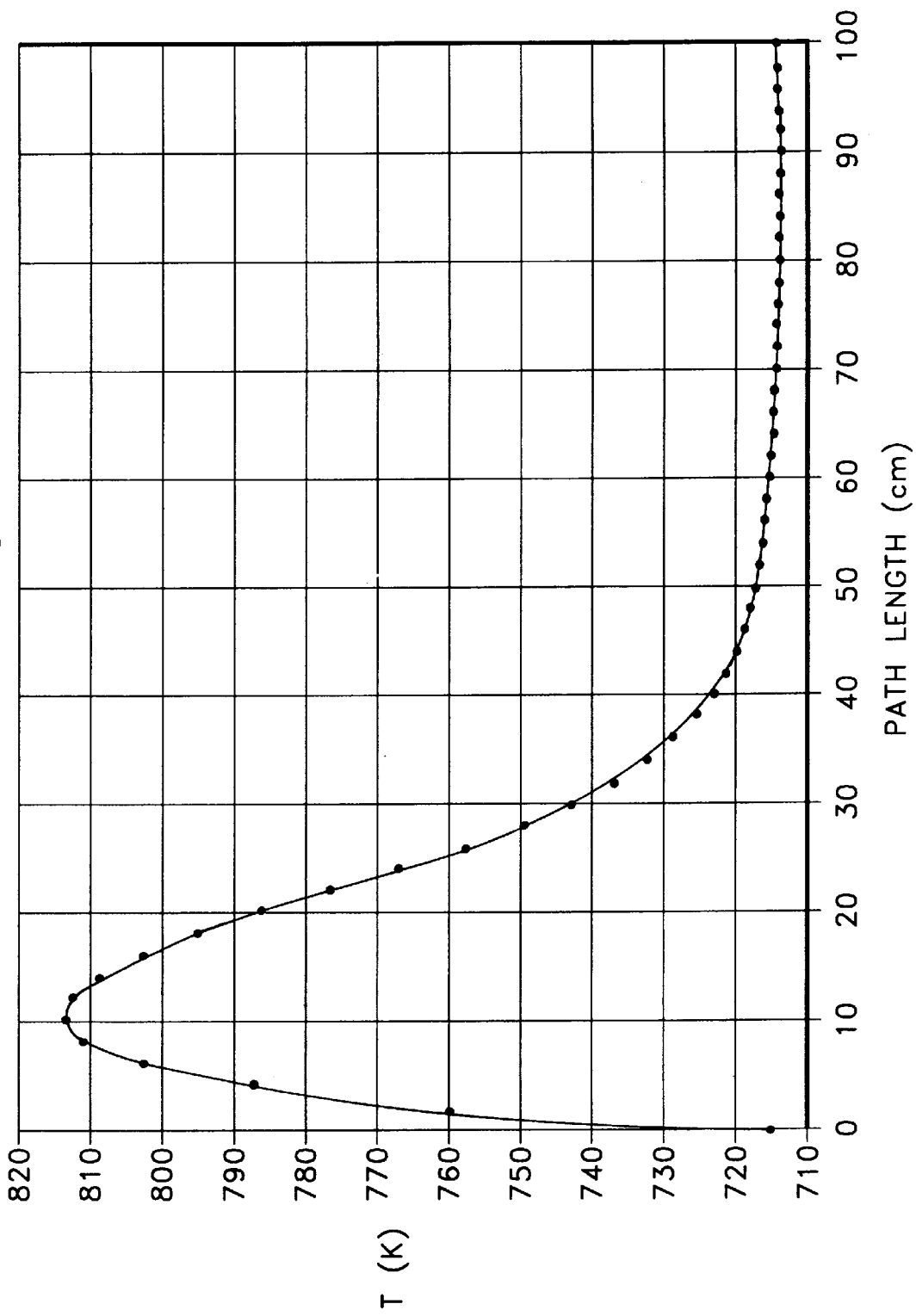
FIGS. 13 through 16 are graphs showing the temperature profile and conversion parameters along the path length of channels in plate heat exchange reactor arrangements for producing PA by orthoxylene oxidation.
Figure 14:
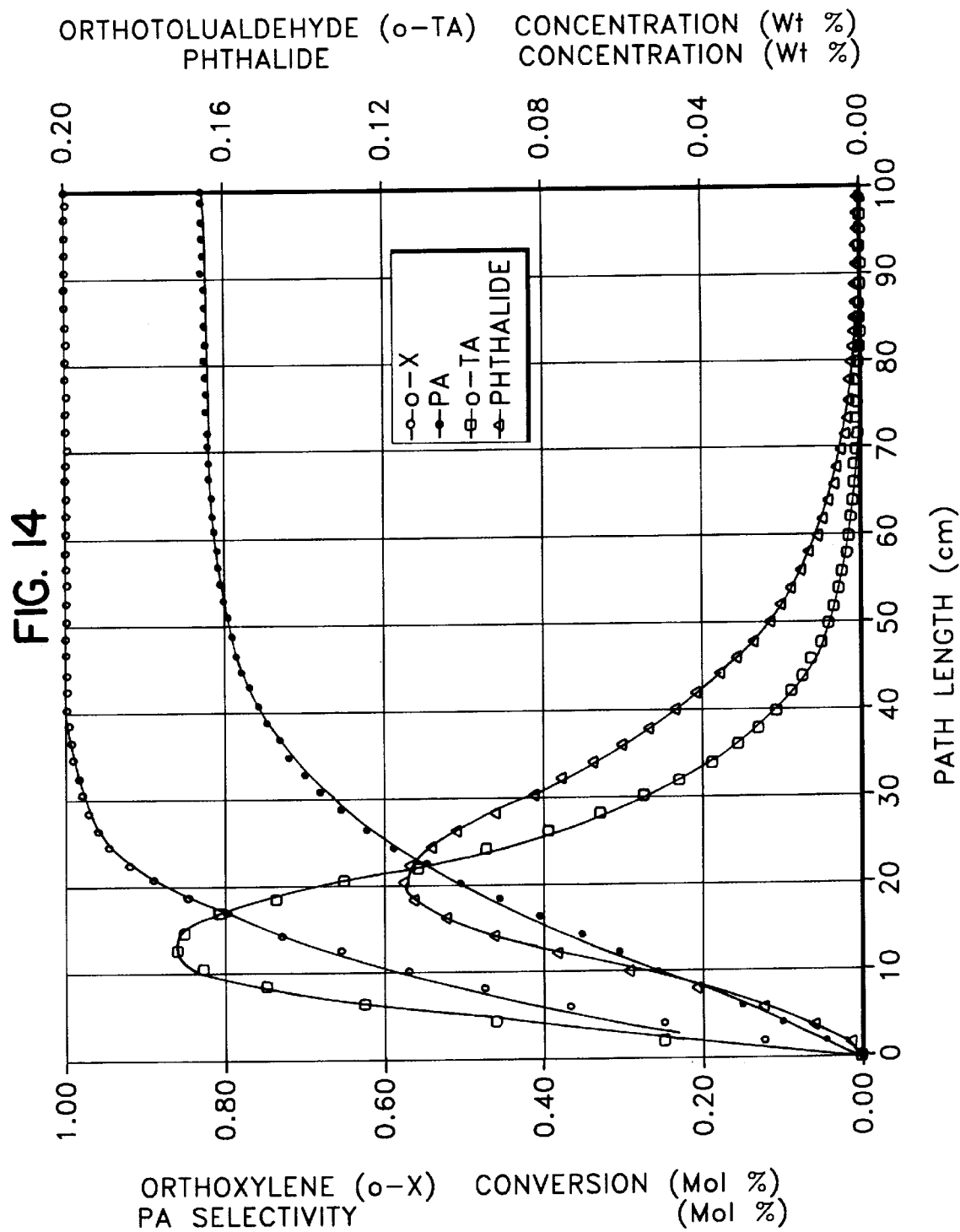

The plate heat exchanger type reactor operates at the same orthoxylene inlet concentration and mass flux through the heat exchange channels as the tubular reactor. The channel arrangement contains a 2 mm spherical catalyst in a 6 mm gap between channels. To maintain a the same 0.3 bar pressure drop across the channels as across the tubes, the process flux in the plate reactor arrangement drops to 7500 kg/m²/hr. Nevertheless, the sizing of the plate exchange reactor maintains the same ratio of heat transfer surface area to catalyst surface area on a per reactor volume basis as in the tubular reactor arrangement. At the same 75 g/Nm³ concentration of orthoxylene in the air feed, the process inlet temperature in the plate exchanger reactor increases 15° C. above the tubular reactor case or to a temperature of about 713° K. to maintain the same phthalide level in the PA product. Even with an increased inlet temperature FIG. 13 shows the peak temperature in the channels decreasing to about 815° C., representing about a 20° C. temperature drop relative to the tubular reactor case. Again, FIG. 14 shows a rapid conversion of orthoxylene along the path length of the plate exchange reactor with about the same selectivity to PA and orthotolualdehyde and phthalide to levels below 1000 ppm. Thus, the temperature reduction of this example demonstrates that the plate heat exchange reactor has about a 30% overall greater heat transfer ability than the tubular reactor.

EXAMPLE 4

Figure 15:
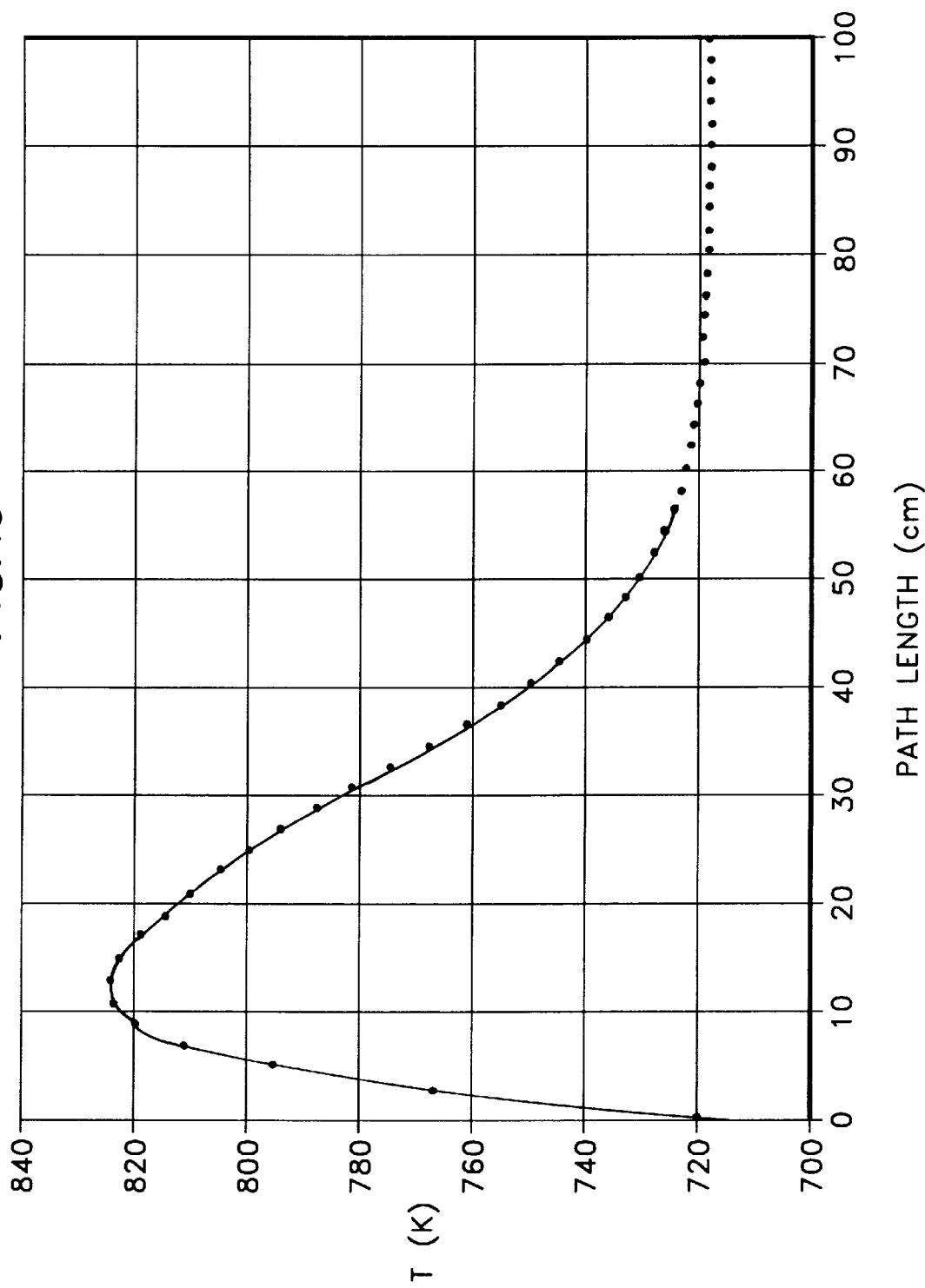
Figure 16:
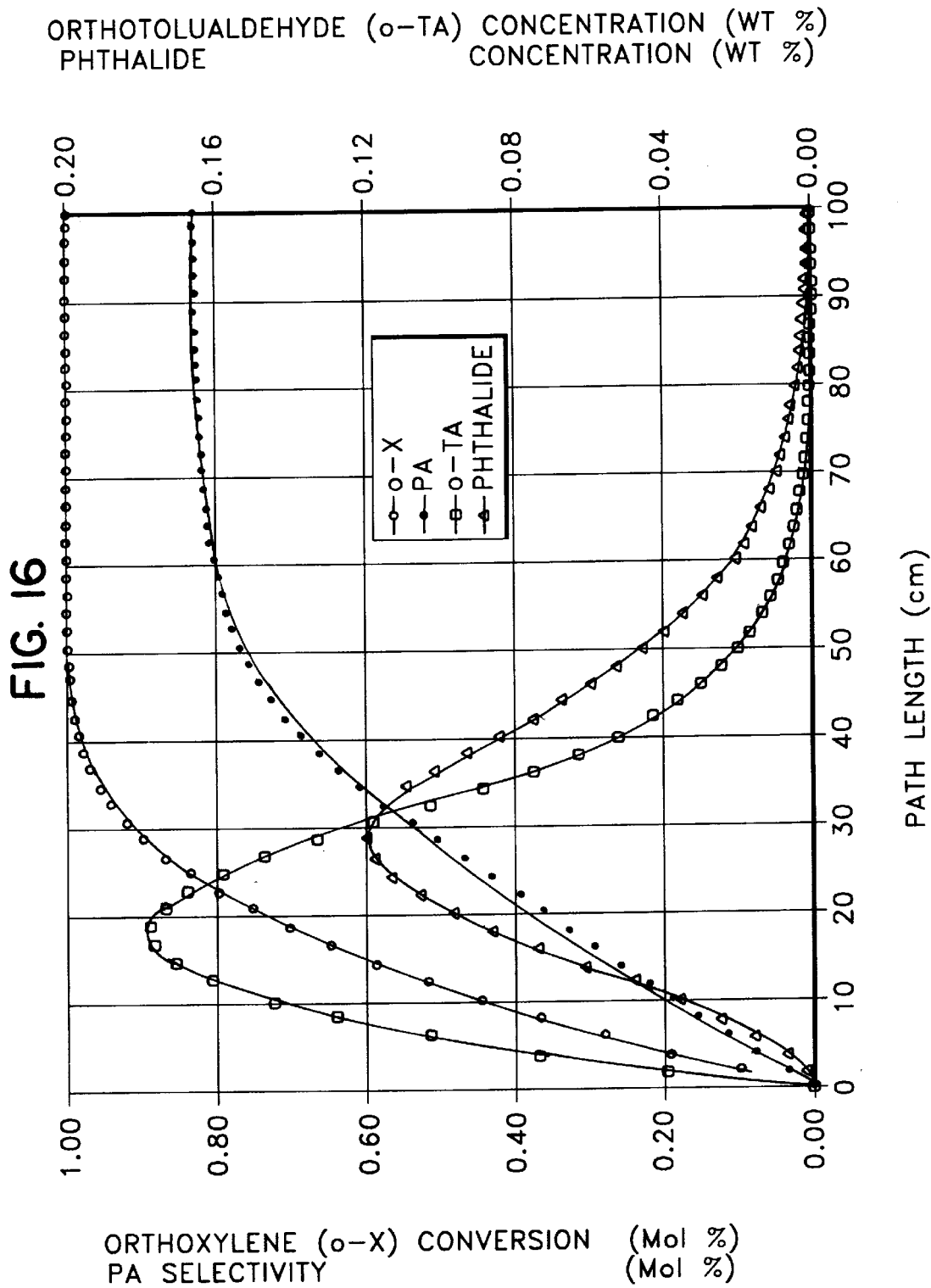

Example 4 evaluates increases in the concentration of the orthoxylene in the air to the plate exchange reactor over the range of from 75 g/Nm³ to 110 g/Nm³.to determine the concentration that produces the same peak temperature in the plate heat exchange reactor as in the tubular reactor. Heat from the additional orthoxylene oxidation requires increasing the circulating salt temperature from the 713° K. in Example 2 to about 717° K. to keep the phthalide concentration below 1000 ppm in the PA product. At a concentration level of about 105 g/Nm³, the peak temperature of the plate reactor (see FIG. 15) approaches the maximum temperatures of the tubular reactor arrangement. As established by FIG. 16, the maximum orthoxylene concentration can increase significantly over the tubular case reactor by use of the plate exchanger while still maintaining the PA selectivity of about 83 mol %.

Overall the examples establish numerous process advantages of the plate reactor arrangement over the tubular reactor arrangement. A comparison of the examples shows the overall added heat efficiency of using a plate heat exchange reactor arrangement that introduces a mixture of air and othoxylene at a single inlet point for the production of phthalic anhydride. Using the plate reactor arrangement with a an increasing orthoxylene concentration in the air at the single feed inlet produces additional advantages. The use of multiple feed injection of the orthoxylene in the plate reactor arrangement can further reduces the plate reactor arrangement costs.

What is claimed is:

1. A process for contacting reactants with a catalyst in a reaction zone and indirectly heating or cooling the reactants by contact with a heat exchange liquid having a high heat capacity, the process comprising:

a) passing a reactant stream through a plurality of narrow reaction channels defined by principal spaced apart plates and establishing a first pressure gradient through the narrow reaction channels;

b) chemically reacting the reactant stream in at least a portion of the narrow reaction channels to produce a reacted stream;

c) passing a liquid heat exchange fluid having a Pr of not more than 0.1 through a plurality of narrow heat exchange channels defined by the principal plates and having a packing contained therein to increase pressure drop and establish a second pressure gradient through the narrow heat exchange channels;

d) indirectly exchanging heat with the reactant stream across the plates in said portion of the reaction channels;

e) maintaining a positive pressure differential from the reaction channels to the heat exchange channels at all locations across the principal plates; and, f) recovering the reacted stream from the reaction channels.

2. The process of claim 1 wherein the positive pressure differential does not exceed 50 psi.

3. The process of claim 1 wherein the principal plates define alternate reaction channels and heating channels.

4. The process of claim 2 wherein the heat exchange liquid and reactant stream pass through the reaction channels and the heat exchange channels in a relative cocurrent flow direction.

5. The process of claim 1 wherein the packing material comprises inert spheres.

6. The process of claim 1 wherein the plates define corrugation and the corrugations maintain the spacing of the plates that define the channels.

7. The process of claim 1 wherein at least a portion of the reaction channel contains a catalyst and the catalyst comprises a particulate material retained in the channels.

8. The process of claim 1 wherein the reaction channels have an average width of less than 1 inch.

9. The process of claim 1 wherein the reaction channels have an average width greater than the width of the heat exchange channels.

10. A process for contacting reactants with a catalyst in a reaction zone and indirectly heating or cooling the reactants by contact with a heat exchange liquid having a high heat capacity, the process comprising:

a) passing a reactant stream through a plurality of narrow reaction channels defined by principal spaced apart plates and into contact with catalyst particles retained in at least a portion of the reaction channels to produce a first pressure gradient through the narrow reaction channels of at least 20 psi;

b) catalytically reacting the reactant stream in at least a portion of the narrow reaction channels to produce a reacted stream;

c) passing a liquid heat exchange fluid having a Pr of not more than 0.1 through a plurality of narrow heat exchange channels defined by the principal plates to interleave the reaction channels and containing a packing material to produce a second pressure gradient through the heat exchange channels that is less than the pressure gradient through the reaction channels;

d) indirectly exchanging heat with the reactant stream across the plates in said portion of the reaction channels;

e) maintaining a positive pressure differential of less than 50 psi from the reaction channels to the heat exchange channels at all locations across the principal plates; and, f) recovering the reacted stream from the reaction channels.

11. The process of claim 10 wherein the heat exchange liquid and reactant stream pass through the reaction channels and the heat exchange channels in a relative cocurrent flow direction.

12. The process of claim 11 wherein the packing material comprises inert spheres.

13. The process of claim 1 wherein the plates define corrugation and the corrugations maintain the spacing of the plates that define the channels.

14. The process of claim 1 wherein secondary plates extend through the reaction channels to increase the average width of the reaction channels relative to the heat exchange channels.

* * * * *